(12) United States Patent
Havlicek et al.

(10) Patent No.: US 6,221,873 B1
(45) Date of Patent: Apr. 24, 2001

(54) CYCLIN DEPENDENT KINASE INHIBITOR

(75) Inventors: Libor Havlicek, Prague; Miroslav Strnad; Marian Hajduch, both of Olomouc, all of (CZ)

(73) Assignee: Institute of Experimental Botany of the Academy of Sciences of the Czech Republic, Prague (CZ)

( * ) Notice: Subject to any disclaimer, the term of this patent is extended or adjusted under 35 U.S.C. 154(b) by 0 days.

(21) Appl. No.: 09/034,581

(22) Filed: Mar. 4, 1998

(51) Int. Cl.$^7$ .................................................. A61K 31/52
(52) U.S. Cl. ................................................... 514/261
(58) Field of Search .............................................. 514/261

(56) References Cited

U.S. PATENT DOCUMENTS 5,866,702   2/1999   Mackman et al. .................... 544/277

FOREIGN PATENT DOCUMENTS

WO9720842
A1   *   6/1997   (WO) .................................. 514/261

OTHER PUBLICATIONS

De Azevedo, Walter et al. (1997) Inhibition of Cyclin–Dependent Kinases By Purinie Analogues Crystal Structure of Human cdk2 Complexed With Roscovitine Eur. J. Bichem, vol. 243, pp. 518–526.

Grant S., et al. (1998) Crystal Structure–Based Dessign of Cyclin Dependent Kinase Inhibitors Proceedings of the American Associate for Cancer Research, vol. 39, No. 1207, p. 176.

Havlicek, Libor et al. (1997) "Cytokinin–Derived Cyclin–Dependent Kinase Inhibitors: Synthesis and cdc2 Inhibitory Activity of Olomoucine and Related Compounds" J. Med. Chem., vol. 40, pp. 408–412.

Hajduch, M. et al. (1997) "Olomoucine Derived Synthetic cdk Inhibitiors: The Mechanisms of Apoptotic Death of Tumor Cells and In Vivo Anti–tumor Activity" Poster Presentation at Cell Cycle Therapeutics Conference, Nov. 6–7, 1997 Washington DC.

Hajduch, M et al. (1997) "Olomoucine Derived Synthetic cdk inhibitors: Induction of Apoptosis and Regression of Spontaneous Dog Melanoma Following In Vivo Application of Olomoucine" Poster Presentation at Cell Cycle Therapeutics Conference, Nov. 6–7, 1997 Washington DC.

Iseki, H. et al. (1997) "A Novel Strategy To Inhibiting Growth of Human Pancreatic Cancer Cells By Blocking Cyclin–Dependent Kinase Activity" Gastroenterology 112 (4 Suppl) No. A1451.

Iseki, Hideaki et al. (1997) "Cyclin–Dependent Kinase Inhibitors Block Proliferation of Human Gastric Cancer Cells", Surgery, vol. 122, No. 2, pp. 187–195.

Kovarova, H. et al. (1997) "Olomoucine Derived Syntheitc CDK Inhibitors: Treatment Induced Dynamic Changes of Cellular Composition in HL–60 Cell Line", Poster Presentation at Cell Cycle Therapeutics Conference, Nov. 6–7, 1997 Washington, DC.

Krucher, Nancy et al. (1997) "The Cyclin–Dependent Kinase (cdk) Inhibitors, Olomoucine and Roscovitine, Alter The Expression of a Molluscan Circadian Pacemaker", Cellular and Molecular Neurobiology, vol. 17, No. 5, pp. 495–507.

Legraverend, Michel et al. (1998) "Synthesis of C2 Alkynylated Purines, A New Family Of Potent Inhibitors of Cyclin–Dependent Kinases" Bioorganic & Medical Chemistry Letters 8, p. 793–798.

Maas, James et al. (1998) "Apoptosis of Central and peripheral Neurons Can Be Prevented With Cyclin–Dependent Kinase/Mitogen–Activated protein Kinase Inhibitors" J. Neurochem., vol. 70, No. 4, pp. 1401–1410.

Meijer, Laurent et al. (1997) "Biochemical and Cellular Effects of Roscovitine, A Potent and Selective Inhibitor of the Cyclin–Dependent Kinases cdc2, cdk2 and cdk5" Eur. J. Biochem, vol. 243, pp. 527–536.

Mgbonyebi, Ozuem, et al. (1998) "Roscovitine Inhibits the Proliferative Activity of Immortal and Neoplastic Human Breast Epithelial Cells", Anticancer Research, vol. 18, pp. 751–756.

Pippin, Jeffrey et al. (1997) "Direct In vivo Inhibition of the Nuclear Cell Cycle Cascade In Experimental Mesangial Proliferative Glomerulonephritis With Roscovitine, A Nvel Cyclin–Dependent Kinase Antagonist" J. Clin. Invest., vol. 100, No. 10, pp. 2512–2520.

Planchais, Severine et al. (1997) "Roscovitine, A Novel Cyclin–Dependent Kinase Inhibitor, Characterizes Restriction Point and G2/M Transition In Tobacco BY–2 Cell Suspension" The Plant Journal vol. 12, No. 1, pp. 191–202.

Rudolph, Bettina et al. (1996) "Activation of Cyclin–Dependent Kinases By Myc Mediates Induction of Cyclin A, But Not Apoptosis" The EMBO Journal, vol. 15, No. 12, pp. 3065–3076.

Schutte, Bert et al. (1997) "The Effect of The Cyclin–Dependent Kinase Inhibitor Olomoucine On Cell Cycle Kinetics" Experimental Cell Research, vol. 236, pp. 4–15.

(List continued on next page.)

*Primary Examiner*—Jerome D. Goldberg
(74) *Attorney, Agent, or Firm*—Lahive & Cockfield, LLP; Giulio A. DeConti, Jr.; Megan E. Williams

(57) ABSTRACT

The present invention is based on the method of treating a patient suffering from leukemia comprising administering a therapeutically effective amount of the compound 2-([(3-hydroxypropyl)amino]-6-benzylamino)-9-isopropylpurine or a pharmaceutically acceptable salt thereof.

15 Claims, 3 Drawing Sheets

OTHER PUBLICATIONS

Figure 1A:
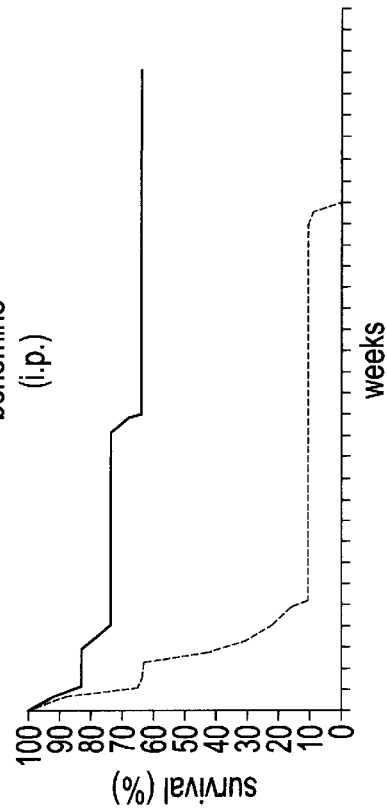

Van Engeland, Manon et al. (1997) "Plasma Membrane Alterations and Cytoskeletal Changes In Apoptosis" Experimental Cell Research, vol. 235, pp. 421–430.

Vesley, Jaroslav et al. (1994) "Inhibition of Cyclin–Dependent Kinases By Purine Analogues", Eur. J. Biochem, vol. 224, pp. 771–786.

Yakisich, J. Sebastian et al. (1998) "Early Inhibition of DNA Synthesis In The Developing Rat Cerebral Cortex By The Purine Analogues Olomoucine and Roscovitine" biochemical and Biophysical Research Communications, vol. 243, pp. 674–677.

* cited by examiner

P388D1 leukemia
isopentenyladenine
(i.p.)

P388D1 leukemia
bohemine
(i.p.)

P388D1 leukemia
olomoucine
(i.p.)

P388D1 leukemia
roscovitine
(i.p.)

B16 melanoma
isopentenyladenine
MST=22.6 days
p=0.759

B16 melanoma
bohemine
MST=28.7 days
p=0.003

B16 melanoma
olomoucine
MST=26.17 days
p=0.014

B16 melanoma
roscovitine
MST=25.9 days
p=0.054 cdk4 activity
in vitro cdk7 activity
in vitro cdk4 activity
in vivo cdk7 activity
in vivo

CYCLIN DEPENDENT KINASE INHIBITOR

RELATED INFORMATION

The contents of Appendix A entitled "Cyclin Dependent Kinase Inhibitor" is expressly incorporated by reference.

The invention relates to the therapeutic uses of the compound 2-([(3-hydroxypropyl)amino]-6-benzylamino)-9-isopropylpurine and pharmaceutically acceptable salts thereof.

It has been observed that this compound is of particular benefit in the treatment of proliferative diseases such as cancers and leukemia's. As described below it has been observed to possess a mechanism of action not previously reported that provides it with particular benefits, for example, it has been shown to inhibit cell proliferation in a manner that does not induce changes in gene transcription i.e. it functions at a level in the cell cycle regulatory control system that does not involve the regulation of gene expression.

The prior art has described several compounds that are capable of regulating the cell cycle by virtue of inhibiting cyclin dependent kinases. These compounds include butyrolactone, flavopiridol and 2-(2-hydroxyethylamino)-6-benzylamino-9-methylpurine (olomoucin). Olomucin and related compounds have been shown to be inhibitors of cdc2. cdc2 (also known as cdk1) is a catalytic sub-unit of a family of cyclin dependent kinases that are involved in cell cycle regulation.

These kinases comprise at least two sub-units, namely a catalytic sub-unit (of which cdc2 is the prototype) and a regulatory sub-unit (cyclin). The cdk's are regulated by transitory association with a member of the cyclin family: cyclin A (cdc2, cdk2), cyclin B1-B3 (cdc2), cyclin C (cdk8), cycline D1-D3 (cdk2-cdk4-cdk5-ckd6), cyclin E (cdk2), cyclin H (cdk7).

Each of these complexes is involved in a phase of the cellular cycle. cdk activity is regulated by post-translatory modification, by transitory associations with other proteins and by modifications of their intra-cellular localization. The cdk regulators comprise activators (cyclins, cdk7/cyclin H, cdc25 phosphateses), the $p9^{CKS}$ and $p15^{cdk-BP}$ sub-units, and the inhibiting proteins ($p16^{INK4A}$, $p15^{INK4B}$, $p21^{Cip1}$, p18, $p27^{Kip1}$).

There is now considerable support in the literature for the hypothesis that cdk's and their regulatory proteins play a significant role in the development of human tumors. Thus, in numerous tumors a temporal abnormal expression of cyclin-dependent kinases, and a major de-regulation of protein inhibitors (mutations, deletions) has been observed.

It has now been observed that the compound 2-([(3-hydroxypropyl)amino]-6-benzylamino)-9-isopropylpurine is a potent in vivo inhibitor of cdk2, cdk4 and cdk7, properties that provide significant advantages in that this compound is capable of inhibiting cell proliferation in proliferating tissue and not healthy tissue and furthermore is capable of inducing apoptosis (programmed cell death) in proliferative cells.

The present invention therefore relates to a method of treating a patient suffering from leukemia comprising administering a therapeutically effective amount of the compound 2-([(3-hydroxypropyl)amino]-6-benzylamino)-9-isopropylpurine or a pharmaceutically acceptable salt thereof.

A further aspect of the present invention relates to a method of treating a patient suffering from cancer comprising administering a therapeutically effective amount of the compound 2-([(3-hydroxypropyl)amino]-6-benzylamino)-9-isopropylpurine or a pharmaceutically acceptable salt thereof.

In a further embodiment the present invention relates to a method of treating a cancerous or leukemic proliferative disease comprising inhibiting the cdk4 and/or cdk7 enzymes by the administration of a therapeutically effective amount of the compound 2-([(3-hydroxypropyl)amino]-6-benzylamino)-9-isopropylpurine or 2-[(1-ethyl-2-hydroxyethyl)amino]-6-benzylamino-9-isopropylpurine or pharmaceutically acceptable salt thereof.

In an additional embodiment the present invention relates to a method of inducing cell death in proliferative cells comprising administering a therapeutically effective amount of the compound 2-([(3-hydroxypropyl)amino]-6-benzylamino)-9-sopropylpurine or 2-[(1-ethyl-2-hydroxyethyl)amino]-6-benzylamino-9-isopropylpurine or pharmaceutically acceptable salt thereof.

In these aspects and embodiments, the proliferative cells may be cancer or leukemic cells and the cancer or leukemia is preferably p53 independent.

The compound of the present invention can be present as a salt, in particular pharmaceutically acceptable salts. These are formed, for example, with strong inorganic acids, such as mineral acids for example sulfuric acid, phosphoric acid or hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as($C_1$–$C_4$)-alkyl- or arylsulfonic acids which are unsubstituted or substituted, for example by halogen, for example methane- or p-toluene sulfonic acid.

The present invention also relates to pharmaceutical compositions comprising 2-([(3-hydroxypropyl)amino]-6-benzylamino)-9-isopropylpurine or a pharmaceutically acceptable salt thereof together with at least one a pharmaceutically acceptable excipient.

The pharmaceutical compositions of the present invention may be adapted for oral, rectal, vaginal, paraenteral, intramuscular, intra-peritoneal, sub-cutaneous intravenous, nasal or buccal routes of administration.

For oral administration, particular use is made of compressed tablets, pills, tablets, gellules, drops and capsules. These compositions advantageously contain from 1 to 100 mg, and preferably from 10 to 40 mg, of active ingredient per dose.

Other forms of administration comprise solutions which can be injected intravenously, sub-cutaneously or intramuscularly, and which are prepared from sterile or sterilisable solutions. They can also be in the form of suppositories, pessaries, suspensions, emulsions, lotions, ointments, creams, gels and sprays.

Injectable forms may contain between 1 and 50 mg, preferably between 10 and 30 mg, of active ingredient per dose.

Compositions may be formulated in unit dosage form, i.e., in the form of discrete portions containing a unit dosage, or a multiple or sub-unit of a unit dose.

By way of example, the posology which can be used in man corresponds to the following doses: thus, for example, a patient will be administered one or more doses of 10 to 50 mg/day for the treatment of tumors.

The following invention is further illustrated by the following examples, which should not be construed as further limiting. The contents of all references, pending patent applications and published patents, cited throughout this application are hereby expressly incorporated by reference. The contents of WO97/20842 (PCT/FR96/01905) are also incorporated herein by reference.

EXAMPLES

Example 1

Preparation of 2-([(3-hydroxypropyl)amino]-6-benzylamino-9-isopropylpurine (bohemine)

Materials and Methods

Melting points were determined on a Kofier block and are uncorrected. Evaporations were carried out with a rotary evaporator under water-pump vacuum or rotary oil pump in the case of dimethyl sulfoxide and amines. The $^1$H NMR spectra (δ, ppm; J, Hz) were measured on Varian VXR-400 (400 MHz) or on Varian Unity 200(200 MHz). All spectra were obtained at 25° C. using tetramethylsilane as internal standard. Electron impact mass spectra (m/z, rel. %) were measured on a VG 7070E spectrometer (70 e/V 200° C., direct inlet) or on a Finnigan MAT 90 spectrometer (70 eV, 250° C., direct inlet) or on a Jeol JMS-D100(80 eV, 200° C., direct inlet). High resolution measurement were carried out by the peak-matching method using Ultramarck 1600F(PCR Inc., Fla., USA) as a standard. The instrument was tuned to a resolution of 8,000 (10% valley definition). Infrared spectra were recorded on a FTIR Nicolet 205 instrument as KBr disks. Merck silica gel Kieselgel 60 (230–400 mesh) was used for column chromatography. TLC was carried out on Merck DC Alufolien Kieselgel 60 F254 plates.

6-Benzylamino-2-chloro-9-isopropylpurine (2)

A mixture of 6-benzylamino-2-chloropurine (1) 1.32 g, 5.08 mmol), potassium carbonate (4.3 g, 31 mmol) and isopropylbromide (5.5 ml, 58 mmol) in 35 ml of dry dimethyl sulfoxide was vigorously shaken overnight. The reaction mixture was evaporated in vacuum and then partitioned between water and ethylacetate. The organic layer was dried (sodium sulfate) and evaporated. Crystallization from methanol afforded 1.305 g (85%) of product 2, m.p. 181–182° C. For C15H16N5Cl(301.78) calculated: 59.70% C, 5.34% H, 23.21% N, 11.75% Cl; found: 59.52% C, 5.36% H, 23.01% N. FTIR spectrum (cm$^{-1}$): 1713, 1626, 1572, 1537, 1497, 1471, 1456, 1425, 1398, 1355, 1314, 1292, 1255, 1228, 1202. $^1$H NMR (400 MHz, (CH3)2SO): 1.48D (6H, J=6.8, (C$\underline{H}$3)2CH); 4.57 m (1H, C$\underline{H}$(CH3)2); 4.66bd (2H, J=6.1, CH2); 7.19 ft, (1 H, J=7.2, J=1.7, H-p); 7.27dd (2H, J=7.2, H-m); 7.34dd (2H, J=7.2, J=1.7, H-o); 7.69s (1 H, H-C$^8$).

2-[(3-hydroxypropyl)amino]-6-benzylamino-9-isopropylpurine(3)

2-Chloroderivative (2) (0.5 mmol) and 3ml of 3-aminopropanol were heated for 3 hours to 160° C. (sealed ampoule). Excess of the amine was evaporated at a temperature below 70° C. and the residue was purified by column chromatography (stepwise 0; 1; 2% MEOH in CHCl3) and crystallized from diethyl ether afforded the product in 82% yield; m.p. 98–101° C. For C18H24N60 (340.43) calc. 63.51% C, 7.11% H, 24.69% N; found 63.43% C, 7.05% H, 24.60% N, Mass spectrum (Finnigan MAT 90): 341 (21), 340.21 10 (M+-, C18H24N60 calc. 340.2012, 100%), 339 (4), 310 (9), 309 (33), 297 (11), 296 (28), 295 (38), 282 (9), 253 (6), 251 (4), 239 (4), 191 (6), 134 (6), 106 (8), 92 (4), 91 (44), 43 (9), 41 (7). $^1$H NMR (200 MHz, CDC13): 1.53d (6H, J=7, (C$\underline{H}$3)2CH); 1.68–1.81m (2H, CH2C$\underline{H}$2CH2); 3.55–3.71M (4H, CH2N+CH20); 4.62hept (1H, J=7, C$\underline{H}$(CH3)2);4.76bd (2H, J=4.5, CH2Ph); 4.96bt (1H, NHC2); 5.10bs (OH or NH); 6.00bs (NH, or OH), 7.22–7.38m (5H, Ph), 7.47s (1 H, H±C8).

An Alternative Synthesis or 6-benzylamino-2-chloro-9-isopropylpurine (2).

2.6-dichloro-9-isopropylpurine

A mixture of 2,6-dichloropurine 1 g (5,3 mmol), powdered potassium carbonate 2 g (14 mmol) were vigorously stirred in 35 ml DMF. Isopropyliodide 3 ml (30 mmol) was added in five portions within 10 hours. Monitoring of the reaction by TLC (EtOAc/heptaine; 1/1) showed that the reaction was nearly complete.

The principle product was isolated by column chromatography stepwise 20, 30, 40% EtOAc in heptaine; crystalization EtOAc/pentane; yield 0.54 g (44%); m.p. 148–150° C. For C8H8N4C12 Calc: 41.58; H, 3.49; N, 24.25; Cl 30.68. Found: C, 41.29; H, 3.71, N, 24.01. $^1$H NMR(400 MHz, CD30D): 1.67(6H, d, J=6.8, (CH3)2CH), 4.93(1H, mt, CH(CH3)2), 8.67(1H, s, H__C8). $^{13}$C NMR(100 MHz, CD30D): 22.74Qqd (J=128.0, J=4.6, J=4.6), 50.79 Dsep (J=143.4, J=4.4), 132.41d (J=11.6)147.67 Dd(J=214.0, J=4.4), 152.24 s, 153.91 s, 154.75 br mt.

6-benzylamino-2-chloro-9-isopropylpurine (2)

2,6-dichloro-9-isopropylpurine (1 mmol) and benzylamine (3,5 mmol) were heated with stirring in 3 ml of n-butanol (3 hour, 110° C.). The reaction mixture (after evaporation of n-butanol) was worked up as above for the compound 2, yield 85–90%.

REFERENCES

1. Hocart C. H., Letham D. S., Parker C. W.: Phytochemistry 30,2477 (1991)

Example 2

Biological Activity of 2-[(3-hydroxypropyl)amino]-6-benzylamino-9-isopropylpurine 2.1 In vitro Cytotoxic Activity of Bohemine In vitro MTT-Assay Introduction One of the parameters used as the basis for colorimetric assays is the metabolic activity of viable cells. For example, a microtiter assay which uses the tetrazolium salt MTT is now widely used to quantitate cell proliferation and cytotoxicity. For instance, this assay is used in drug screening programs and in chemosensitivity testing. Because tetrazolium salts are cleaved only by metabolically active cells, these assays detect viable cells exclusively. In the case of MTT-assay, yellow soluble tetrazolium salt is reduced to colored water-insoluble formazan salt. After it is solubilized, the formazan formed can easily and rapidly be quantified in a conventional ELISA plate reader at 570 nm (maximum absorbance). The quantity of reduced formazan corresponds to number of vital cells in the culture.

Materials

Human T-lymphoblastic leukemia cell line CEM, promyelocytic leukemia HL-60, human breast carcinoma cell line MCF-7, cervical carcinoma cells HELA, mouse fibroblasts NIH3T3, mouse immortalized bone marrow macrophages B2.4 and B10A.4, P388D1 and L1210 leukemias, B16 and B16F10 melanoma were used for routine screening of compounds. The cells were maintained in Nunc/Corning 80 cm$^2$ plastic tissue culture flasks and cultured in cell culture medium (DMEM with 5 g/l glucose, 2 mM glutamine, 100 U/ml penicillin, 100 μg/ml streptomycin, 10% fetal calf serum and sodium bicarbonate). The compound roscovotine 2-[(1-ethyl-2-hydroxyethyl)amino]-6-benzylamino-9- isopropylpurine was prepared as described in WO97/20842. The compound 2-[(3-hydroxypropyl)amino]-6-benzylamino-9-isopropylpurine prepared as described above, is hereinafter referred to as bohemine.

Methods

The cell suspensions that were prepared and diluted according to the particular cell type and the expected target cell density (2,500–30,000 cells per well based on cell growth characteristics) were added by pipet (80 µl) into 96 well microtiter plates. Inoculates were allowed a preincubation period of 24 hours at 37° C. and 5% $CO_2$ for stabilization. Four-fold dilutions of the intended test concentration were added at time zero in 20 µl aliquots to the microtiter plate wells. Usually, test compound were evaluated at six 4-fold dilutions. In routine testing, the highest well concentration were 266.7 µM, but it can be modified dependent on the agent. All drug concentrations were examined in duplicate. Incubations of cells with test compounds lasted for 72 hours at 37° C., in 5% $CO_2$ atmosphere and 100% humidity. At the end of incubation period, the cells were assayed by using the MTT. Ten microliters of the MTT stock solution were pipeted into each well and incubated further for 1–4 hours. After this incubation period, formazan was solubilized by addition of 100 µl/well of 10% SDS in water (pH=5.5) followed by further incubation at 37° C. overnight. The optical density (OD) was measured at 540 nm with the Labsystem iEMS Reader MF (UK). The tumor cell survival (TCS) was calculated using the following equation: TCS=($OD_{drug\ exposed\ well}$/mean $OD_{control\ wells}$)× 100%. The $TCS_{50}$ value, the drug concentration lethal to 50% of the tumor cells, was calculated from the obtained dose response curves.

2.2 In vivo Antitumor Activity of Bohemine

To analyze the effects of cytokinine derivatives on growth of transplanted tumors, the models of intraperitoneally transplanted P388D1 leukemia (4×1 mg/day i.p.) and subcutaneously innoculated B16 melanoma were applied.

1. Mouse Melanoma B16

Figure 1C:
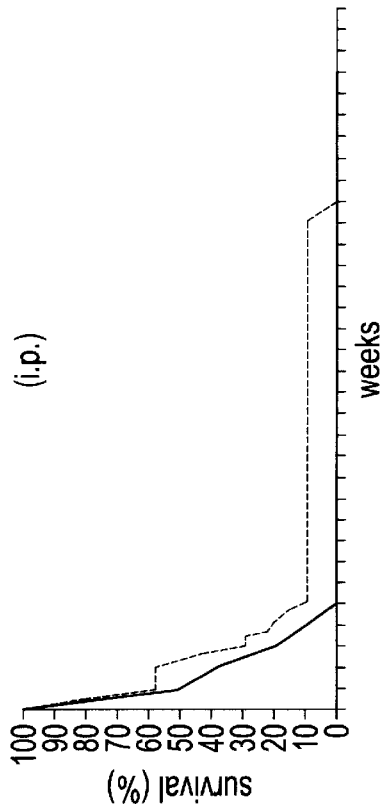
Figure 1B:
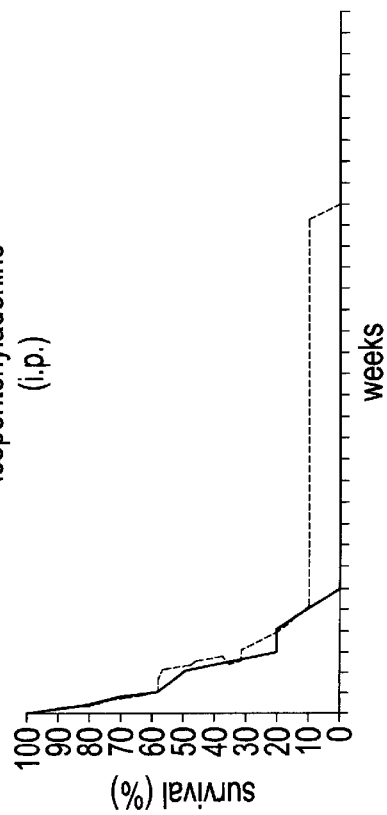
Figure 1D:
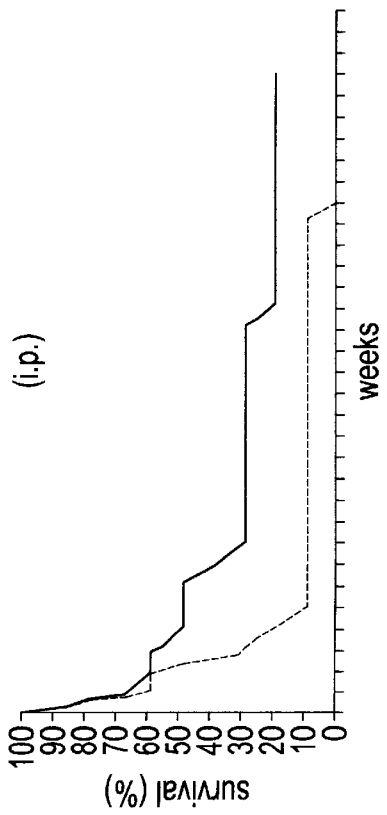
Figure 1E:
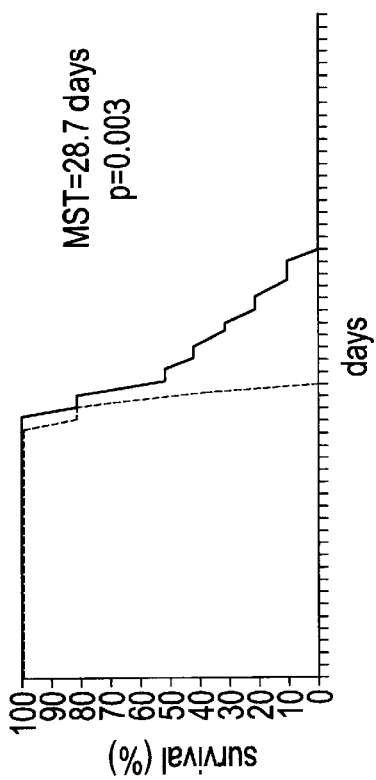
Figure 1G:
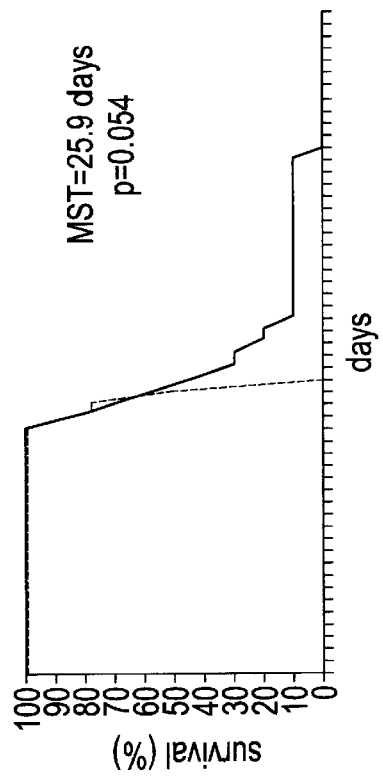
Figure 1F:
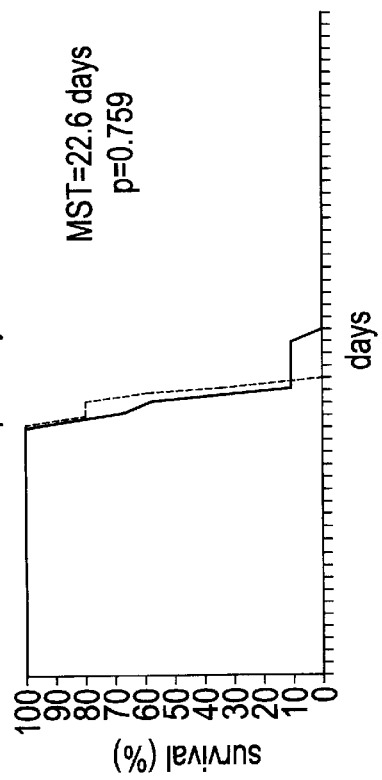
Figure 1H:
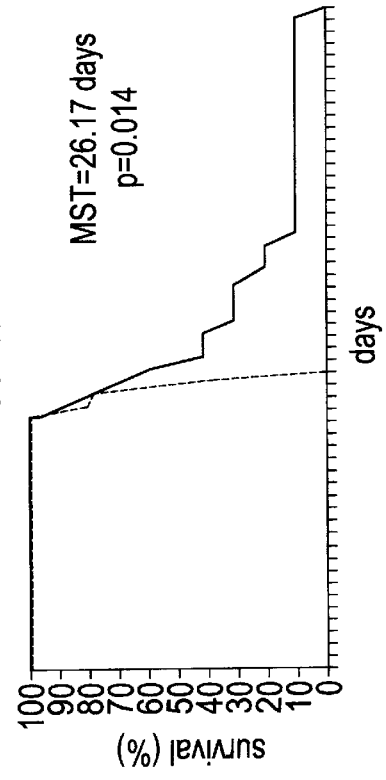

Mouse melanoma cells B16 were grown in DMEM with 5 g/l glucose, 2 mM glutamine, 100 U/ml penicillin, 100 µg/ml streptomycin, 10% fetal calf serum and sodium bicarbonate up to 80% confluency. Cells were trypsinized, washed in PBS and suspended in PBS with 0.5% bovine serum albumin. 0.5 million cells from this suspension was applied subcutaneously to C57BL-10 mice. One day later, animals were treated with vehicle or indicated compounds: isopentenyladenine (IP), olomoucine (OC), bohemine (BOH), roscovitine (ROSC). The compounds (1 mg) were applied subcutaneously 4×daily, for 7 days. Medium survival time (MST) was evaluated in all experimental groups as indicated in FIG. 1.

1. Murine Leukemia P388D1

Mouse P388D1 leukemia was grown in DEM with 5 g/l glucose, 2 mM glutamine, 100 U/ml penicillin, 100 µg/ml streptomycin, 10% fetal calf serum and sodium bicarbonate up to 80% confluency. Cells were scraped, washed in PBS and suspended in PBS with 0.5% bovine serum albumin. 0.5 million cells from this suspension was applied intraperitoneally to DBA-2 mice. One day later, animals were treated with vehicle or indicated compounds: isopentenyladenine (IP), olomoucine (OC), bohemine (BOH), roscovitine (ROSC). The compounds (1 mg) were applied subcutaneously 4×daily, for 7 days. Survival (%) was evaluated in all experimental groups as indicated in FIG. 1.

Formulation materials in vitro cyctotoxicity/antiproliferative assays: 10% dimethylsulfoxide (DMSO), 80 mM HCl in physiological saline (0.9%) w/v sodium chloride) in vivo anti-cancer activity assays. water insoluble compounds: 50% DMSO, 10 mM HCl in saline.

Results 2.1 In vitro cytotoxic activity of bohemine

To evaluate anti-cancer activity of IP, OC, BOH and ROSCa, toxicities of these compounds were tested on panel of cell lines of different histogenetic and species origin (Table 1).

TABLE 1

| | IC50 (µM) | | | | | | | | | | | | |
|---|---|---|---|---|---|---|---|---|---|---|---|---|---|
| | CEM | HL-60 | B16 | B16F10 | MCF7 | HELA | B10#4 | B2#4 | U937 | L1210 | P388D1 | NIH3T3 | Lymphocytes |
| IP | 168.9 | 157.41 | 266.7 | 266.7 | 266.7 | 266.7 | 266.7 | 266.7 | 266.7 | 266.7 | 266.7 | 266.7 | 266.7 |
| OC | 20.68 | 28.9 | 50.4 | 20.6 | 30.53 | 100.4 | 20.26 | 8.1 | 63.8 | 23.5 | 14.5 | 266.7 | 266.7 |
| BOH | 6.16 | 16.7 | 22.6 | 4.3 | 17.0 | 11.1 | 8.3 | 6.4 | 20.1 | 12.8 | 6.3 | 266.7 | 266.7 |
| ROSC | 4.3 | 11.7 | 15.8 | 4.0 | 5.27 | 7.55 | 15.9 | 6.9 | 19.4 | 8.7 | 5.8 | 266.7 | 266.7 |

We show here that equal activities were found in all tumor cell lines tested, however, the non-malignant cell, e.g. NIH3T3 fibroblasts and normal human lymphocytes, were resistant to synthetic CDKI induced toxicity. As demonstrated in Table 1, IP did not show significant toxicity, OC was moderately effective, while BOH and ROSC killed tumor cells in concentrations close to 10–20 µM.

2.2 In vivo antitumor activity of bohemine

However, in contrast to in vitro assays, only olomoucine and bohemine showed significant in vivo activity in both mouse P388D1 leukemia and B16 melanoma models (FIG. 1). Isopentenyladenine showed no activity and toxicity in vivo, while roscovitine was inactive and, moreover, its application resulted in induction of deep skin/peritoneal necrotic lesions after subcutaneous/intraperitoneal application. These results indicate that enzyme inhibitory activity and in vitro cytotoxicity of CDKIs does not automatically predict anti-cancer activity.

Example 3

The effect of olomoucine derived synthetic CDKIs on cdk4 and cdk7 activities under in vitro and in vivo conditions Introduction Cyclin dependent kinases require association with cyclin and phosphorylation on Thr 160/161 for they activity. Cdk 7 was previously identified as an enzyme necessary for this activating phosphorylation. Initial studies on olomoucine derived synthetic CDKIs showed that these compounds inhibit cell cycle progression in late G1 phase. Since the activation of cdk4/cdk6 kinases is required for cancer cells to pass the G1 restriction point, we have examined the ability of our compounds to inhibit cdk4 kinase under both in vitro and in vivo conditions. In agreement with previous observations, cdk4 was not inhibited with olomoucine derivatives in vitro (IC50>250 µM) (see Table 2 of WO97/20842), while the activity of cdk4 immunoprecipitated from the cells treated with the same substances was rapidly decreased. One of the possible explanations was that cytokinine derived CDKIs down regulate the activity of cdk7 and thus protect cdk4 from activating phosphorylation on Thr 161. it is described here for the first time that the compound 2-([(3-hydroxypropyl)amino]-6-benzylamino)-9-isopropylpurine is a potent inhibitor of cdk7 under both in vitro and in vivo conditions where cdk4 inhibition is also observed, and, more generally, this invention implies the application of these family compounds for the treatment of tumors with increased activity of cdk7 and/or cdk4.

Protein Reagents

Baculovirus encoded human cdc2 and cyclin B1, (kind gift of Dr. David Lane) were expressed in Sf9 cells as described elsewhere. Glutathione S-transferase-carboxy terminal retinoblastoma protein (GST-Rb) containing multiple phosphorylation sites for cdk2 and cdk4 (kind gift of Dr. Jiri Bartek) was expressed in E. coli and affinity purified.

For cdk7 activity studies, cdc2/cyclin B1 complex was used as a substrate. Its autocatalytic activity was inhibited by covalent binding of ATP analog 5-p-fluorosulfonylbenzoyladenosine (FSBA) to ATP binding site of the kinase. Briefly, 200 μl of baculovirus lysate containing co-expressed cdc2/cyclin B1 were diluted with 1800 μl of 50 NaCl, 10 mM MgCl$_2$, 1 mg/ml ovalbumin, 10% DMSO, 50 mM potassium-HEPES buffer with protease inhibitors, 200 μl of DMSO containing 20 mM FSBA were added, and the mixture was incubated at room temperature for 30 minutes. Following the incubation period, the mixture quenched by micro-dialysis against EB buffer (15 mM of MgCl$_2$, 20 mM of potassium EGTA, 10 mM of dithiothreitol, 80 mmol of glycerol-2-phosphate, pH 7.3, 1 mM of sodium vanadate, 1 mM of NaF, 1 mM of phenylphosphate, 10 μg/ml of leupeptin, 10 μg/ml of aprotinin, 10 μg/ml of soybean trypsin inhibitor, 100 μmol of benzamide) overnight at room 4° C. The solution of inactive cdc2/cyclin B1 was concentrated to final volume of 200 μl by ultrafiltration and stored at −80° C. until used.

cdk4 activity

Cdk4 protein was immunoprecipitated from log phase growing cells using the anti-cdk4 monoclonal antibody and Protein-G Sepharose as described elsewhere with only one modification, e.g. two final washes were done in the kinase buffer (60 mmol of glycerol-2-phosphate, 15 mmol of p-nitrophenyl phosphate, 125 mmol of MOPS, pH 7.2, 5 mmol of EGTA, 15 mmol of EGTA, 15 mmol of MgCl$_2$, 1 mmol of dithiothreitol, 1 mmol of sodium vanadate, 1 mM of NaF, 1 mmol of phenyl phosphate, 10 μg/ml of leupeptin, 10 μg/ml of aprotinin, 10 μg/ml of soybean trypsin inhibitor, 100 μmol of benzamide) instead of RIPA buffer. Following the final wash, immunoprecipitated cdk4 protein equivalent to $10^6$ cells in kinase buffer was mixtured on ice with 1 μl (10 mg/ml) Rb-GST protein, 15 μmol/γ-$^{32}$P/ATP (3000 μCi/mmol, 1 mCi/ml), 0.3 μl of DMSO or DMSO solubilized tested compounds at appropriate concentrations in total volume of 30 μl. Kinase reaction was performed at 30° C. for 15 minutes and it was interrupted by addition of 7 μl of 5×SDS-PAGE sample buffer. Aliquots of these samples (25 μl) were electrophoresed in 10% polyacrylamide gels, autoradiographed and quantified by densitometry.

cdk7 activity

Cdk7 protein was immunoprecipitated from log phase growing CEM cells using the anti-cdk7 monoclonal antibody and Protein-G Sepharose as described elsewhere, with only one modification, e.g. two final washes were done in the EB buffer instead of RIPA buffer. Following the final wash, immunoprecipitated cdk7 protein equivalent to $10^6$ cells was mixtured on ice with 10 μl of FSBA inactivated cdc2/cyclin B1 complex as a substrate, 3 μl of 1M MgCl$_2$, 15 μmol/γ-$^{32}$P/ATP (3000 μCi/mmol, 1 mCi/ml), and 1 μl DMSO and/or DMSO solutions of tested compounds at appropriate concentrations respectively in total volume of 100 μl of EB buffer. This reaction mixture was incubated at 30° C. and reaction was quenched after 30 minutes by addition of 20 μl 5×SDS-PAGE sample buffer. 25 μl aliquots of the samples were electrophoresed in 12% polyacrylamide gels, autoradiographed and quantified by densitometry.

Results

Figure 2A:
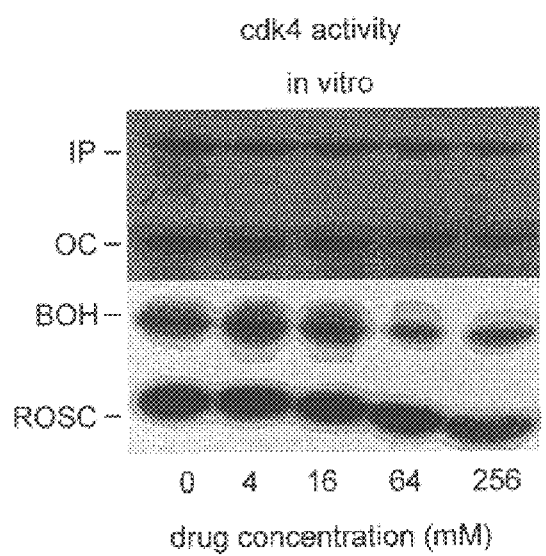
Figure 2B:
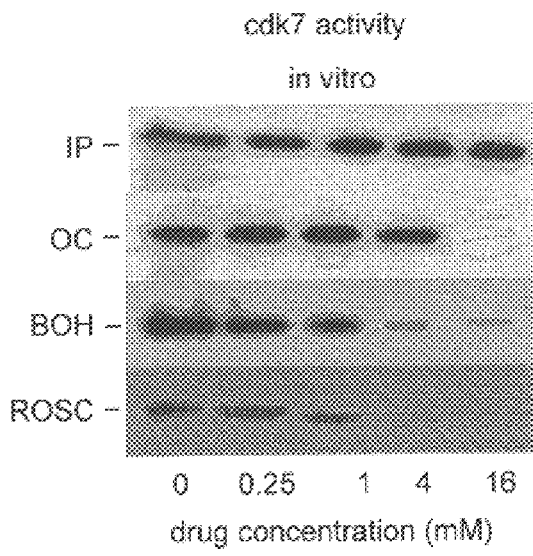
Figure 2C:
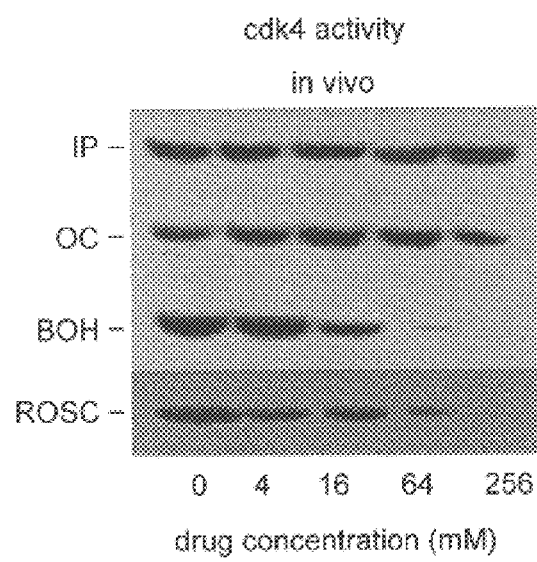
Figure 2D:
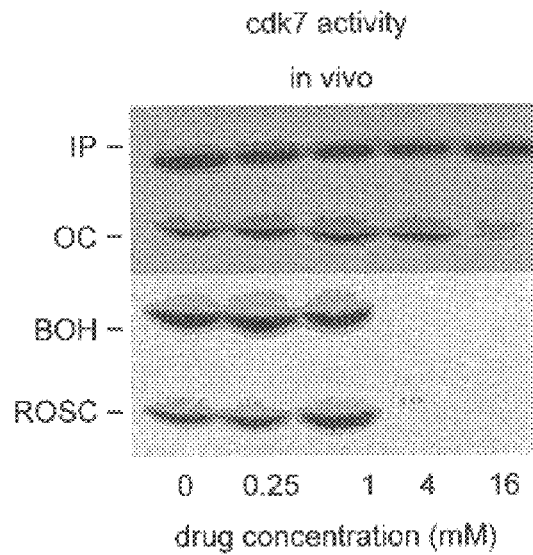

Our results demonstrate that cytokinine derivatives were found to inhibit cdk4 activity in vivo, while the same compounds were entirely ineffective under in vitro conditions (FIG. 2). Despite this observation could be explained by dysregulation of Try 15 dephosphorylation process and cdc25 phosphatase activity, we proved that inhibition of cdk7 is responsible for decrease in cdk4 activity in vivo (FIG. 2). This is the first demonstration of ability of OC derived synthetic CDKIs to inhibit cdk7 kinase under both in vitro and in vivo conditions.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting cdk4 and cdk7 in a cell comprising contacting said cell with an amount of the compound 2-([(3-hydroxypropyl)amino]-6-benzylamino)-9-isopropylpurine or 2-[(1-ethyl-2-hydroxyethyl)amino]-6-benzylamino-9-isopropylpurine or pharmaceutically acceptable salts thereof such that cdk4 and cdk7 enzymes are inhibited in said cell.

2. The method of claim 1, wherein the compound is 2-([(3-hydroxypropyl)amino]-6-benzylamino)-9-isopropylpurine.

3. The method of claim 2, wherein the cell is a leukemia cell.

4. The method of claim 3, wherein the leukemia is not dependent on p53.

5. The method of claim 2, wherein the cell is a cancer cell.

6. The method of claim 5, wherein the cancer is not dependent on p53.

7. The method of claim 2, wherein proliferation of the cell is inhibited.

8. The method of claim 2, wherein cell death is induced.

9. The method of claim 1, wherein the compound is 2-[(1-ethyl-2-hydroxyethyl)amino]-6-benzylamino-9-isopropylpurine.

10. The method of claim 9, wherein the cell is a leukemia cell.

11. The method of claim 10, wherein the leukemia is not dependent on p53.

12. The method of claim 9, wherein the cell is a cancer cell.

13. The method of claim 12, wherein the cancer is not dependent on p53.

14. The method of claim 9, wherein proliferation of the cell is inhibited.

15. The method of claim 9, wherein cell death is induced.

* * * * *